US00PP22300P2

(12) United States Plant Patent
Hurd

(10) Patent No.: US PP22,300 P2
(45) Date of Patent: Dec. 6, 2011

(54) ***HIBISCUS* PLANT NAMED 'SULTRY KISS'**

(50) Latin Name: ***Hibiscus* hybrid (L.)**
Varietal Denomination: Sultry Kiss

(75) Inventor: Kevin A. Hurd, Grand Rapids, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 12/804,429

(22) Filed: Jul. 21, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner* — Kent L Bell

(57) ABSTRACT

The new and distinct plant cultivar of hardy *Hibiscus* named 'Sultry Kiss' comprising heavily branched purple tinted stems containing three-lobed maple-like foliage with burgundy tinting, and flowers with heavily overlapped magenta red petals and crimson red eye, over at least 12 weeks during the summer and early fall until frost.

1 Drawing Sheet

Botanical classification: *Hibiscus* hybrid (L.).
Variety denomination: 'Sultry Kiss'.

BACKGROUND AND ORIGIN OF THE PLANT

The present invention relates to the new and distinct hardy *hibiscus* plant, *Hibiscus* 'Sultry Kiss' hybridized by Kevin A. Hurd in the summer of 2006 at a nursery in Zeeland, Mich. The new Plant, originally assigned the breeder identification number 06-210-01 is a cross between *Hibiscus* 'Fantasia' U.S. Plant Pat. No. 11,853 as the female parent (pod parent) times *Hibiscus* 'Fireball' U.S. Plant Pat. No. 13,634 as the male parent (pollen parent). *Hibiscus* 'Sultry Kiss' has been asexually propagated both by shoot tip stem cuttings and sterile tissue culture at the same nursery in Zeeland, Mich. first since 2008. The resultant plants have been found to be stable and true to type in successive generations of asexual reproduction.

SUMMARY OF THE PLANT

*Hibiscus* 'Sultry Kiss' differs from its parents as well as all other hardy *hibiscus* known to the applicant in many traits. The flower of 'Sultry Kiss' is more ruffled producing heavier substance petals of magenta red with a darker eye of crimson red, whereas 'Fireball' flower is red with a red eye similar to the petal color, and 'Fantasia' is lavender pink with a fuchsia eye. Flower size of 'Sultry Kiss' is intermediate the two parents, larger than 'Fantasia' but not quite as large as 'Fireball'. The petals of 'Sultry Kiss' overlap much more than 'Fireball' and are similar in overlap to those of 'Fantasia'. The flower depth of 'Sultry Kiss' is closer to that of 'Fantasia' whereas 'Fireball' is much flatter. The foliage of 'Sultry Kiss' is a dark green with tinting of purple, similar to 'Fireball' whereas 'Fantasia' has much less purple tinting in the foliage. The foliage shape of 'Sultry Kiss' is variable, depending on the time of year and position on the stem. It is most frequently tri-lobed, but may also be ovate with an acute apex and rarely 5-lobed. Foliage of 'Fantasia' is most often ovate and 'Fireball' most often 5-lobed. The most similar *hibiscus* known to the applicant is 'Lord Baltimore' (not patented) with bright red flowers and green dissected foliage it differs from 'Sultry Kiss' which has a duller red flower and purple tinted foliage. 'Sultry Kiss' also has purple stems compared to the solid green stems of 'Lord Baltimore'. The new plant compares to 'Party Favor' (U.S. Plant patent application Ser. No. 12/804,404) in being magenta red-flowered rather than pink, in having darker purple stems, smaller foliage with less dissection and in having less over-lapping petals with less ruffling.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
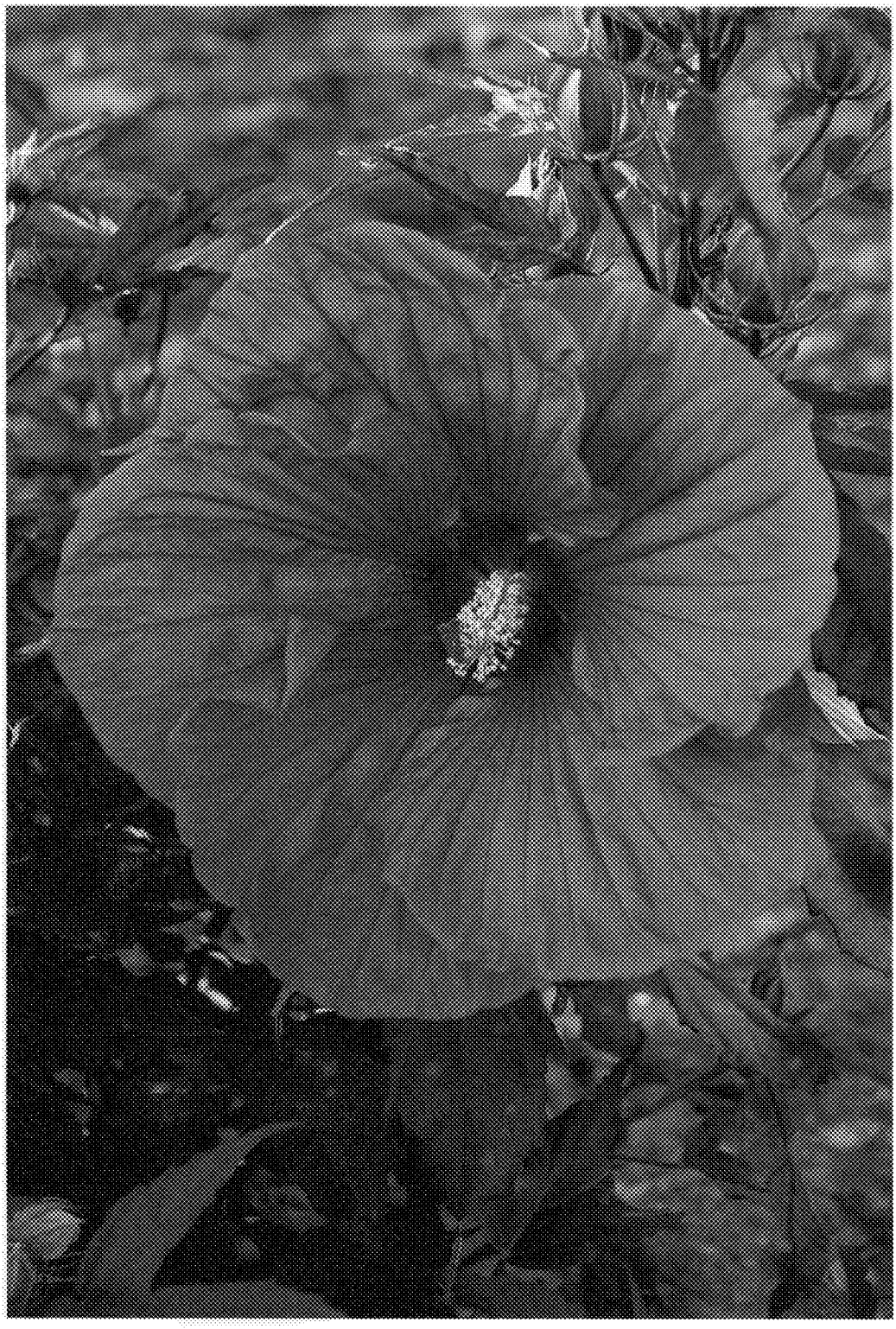
FIG. 1 shows the new plant in flower during the early part of the flowering season.

*Hibiscus* 'Sultry Kiss' is distinct from all other *Hibiscus* known to the applicant in the following combined traits:

1. Heavily overlapped magenta red flower petals with deep crimson eye.
2. Dissected and serrated three-lobed maple-like foliage with purple tinting.
3. Stems heavily branched with dark purple tinting.

DETAILED BOTANICAL DESCRIPTION

The following descriptions and color references are based on the 2001 edition of The Royal Horticultural Society Colour Chart except where common dictionary terms are used. The new plant, *Hibiscus* 'Sultry Kiss', has not been observed under all possible environments. The phenotype may vary slightly with different environmental conditions, such as temperature, light, fertility, moisture and maturity levels, but without any change in the genotype. The following observations and size descriptions are of two-year old and three-year old plants in the trial field of a nursery in Zeeland, Mich. with supplemental fertilizer and water as needed. The plants were not treated with plant grow regulators.

Botanical classification: *Hibiscus* L.×hybrid.

Parentage: *Hibiscus* 'Fantasia' U.S. Plant Pat. No. 11,853 (female) times *Hibiscus* 'Fireball' U.S. Plant Pat. No. 13,634 (male);

Propagation:

*Method.*—Stem cuttings and sterile laboratory tissue culture division.

*Time to initiate roots from tissue culture.*—About two weeks.

*Rooting habit.*—Normal, thick to about 3.5 cm diameter, fleshy, branching; root color creamy white depending on soil type.

*Crop time.*—Under normal summer growing conditions 12 to 16 weeks to flower in a four-liter container from cutting. Plant vigor is very good.

Plant description:

*Plant shape and habit.*—Hardy herbaceous perennial with 5 to 9 thick upright to curved upright branched main stems producing rounded mound; 7 to 12 branches per main stem protruding at 45° to 60° angle from vertical.

*Plant size.*—Unpinched plant with stems 120 to 150 cm tall, average about 132 cm tall from soil line; overall plant 120 to 140 cm wide at the widest point; stem width 2.5 to 3.5 cm at base.

*Internode length.*—Unpinched plant varied between 3.5 to 6.5 cm, average about 4.0 cm.

*Foliage description.*—Opposite; dentate; glabrous (top and bottom); irregularly cleft palmate with lobes cleft about half way to base, rarely 5-lobed and cleft nearly all the way to base; lobes have producing an angle of 45 to 80 degrees from center vein; texture dull above and below; palmately veined; 12 to 18 cm across and 12 to 20 cm long, average 16 cm wide and 16.5 cm long.

*Foliage color.*—Adaxial between RHS 137A and RHS 137B with burgundy tinting between RHS N186B and RHS 187A and palmate veins nearest RHS 60B; abaxial between RHS 138A and RHS 137C with tinting of nearest RHS N186C and veins as light as RHS 27B with green undertones or as pigmented as RHS 187C.

*Petioles.*—5.5 to 10 cm long and 4 to 7 mm wide at base; plano-convex with the top portion flattened; above nearest RHS 182B, below between RHS N170C and lighter than RHS 182D with green undertones of nearest RHS 146D.

Flower description:

*Flowers.*—Solitary, flat, upward and outwardly facing; 22 to 26 cm across, petals opening nearly flat to 2.0 cm deep without column, smaller later in flowering season; persist for a one to two days; effective for at least 12 weeks beginning mid to late July and lasting into October, no detectable fragrance.

*Buds two days prior to opening and showing petals.*—About 6.0 cm long and 3.5 cm in diameter, muticous to acute apex and bluntly rounded base, unopened petals wrinkled at veins, petal color nearest RHS 59A; prior to showing petals buds are ovoid, about 3.5 cm long and 2.5 cm in diameter, with acute apex; ridged along sepal joints; color nearest RHS 144A.

*Epicalyx.*—Entire, smooth, glabrous, linear with sharply acute apex, curved around sepals; 12 to 14 per flower; about 2.3 cm long tapering to base of 2 to 3 mm wide; color nearest RHS 138A on both inner and outer surfaces.

*Sepals.*—Five, proximal half connate forming campanulate star-shaped calyx; acute apex; 4.5 cm long and 2.5 cm wide; outer color nearest RHS 139B with occasional tinting of RHS 183D and inner color nearest RHS 144A; three primary sepal veins nearest the same color as the surrounding sepal tissue on outside and nearest RHS 144D.

*Petals.*—Five; adnate to stamen column at base, overlapping to nearly 100% at widest part of petal (each petal nearly being overlapped by the other two petals on either side); 15.0 to 17.0 cm long and 17.0 to 19.0 cm wide at widest portion; front petal color ranging between RHS 185B and RHS 185C with a 5.0 cm wide darker red eye nearest RHS 187B and palmate veining nearest RHS 185B; back petal color between RHS 185C and RHS 185D; veins palmate, same color as petals on back.

*Gynoecium.*—Style: enclosed in column.

*Column.*—7.0 to 9.0 cm long and 1.5 cm wide at base; column color nearest RHS 60B.

*Style.*—Protruding from column and split into five branches in the distal 7 to 10 mm; color between RHS 60B and RHS 60A.

*Stigma.*—Five; globose, about 3 mm in diameter, nearest RHS 185A.

*Androecium.*—Filaments: numerous, about 120; less than 1 mm in diameter and about 10 mm long; attached to nearly the entire length of column; lighter (more white) than RHS N74D.

*Anthers.*—Reniform; about 2 mm long and 1 mm wide; nearest RHS 185B.

*Pollen.*—Numerous, globose, less than 0.1 mm long, nearest RHS 159C.

*Pedicel.*—Microscopically pubescent; length from base of sepal to abscission point about 2.0 cm long and 4 mm wide on early flowers; flowers are held out easily visible by up to 7.0 cm long from abscission point to stem and 4 mm wide on early flowers shortening to about 3.0 cm distally on stem; color nearest RHS 138A portion distal from abscission layer; proximal to abscission layer nearest RHS 182C with green undertones or nearest RHS 138A.

*Peduncle.*—Branched scape; glabrous, rounded; average 135 cm. tall; 20 to 25 flowers per apical scape without pinching; branched with 7 to 12 branches per main stem; axillary branches having 1 to 7 flowers; average about 60 flowers per stem; color nearest RHS 178B with greenish undertones.

Fruit: Loculicidal capsule; glabrous; globose; occasionally with abruptly acute apex; mature color RHS N199B;

Seed: Minutely floccose, globose to slightly reniform; 3 to 4 mm in diameter; RHS 200A;

Disease resistance: Resistance beyond that of other hardy *hibiscus* cultivars has not been observed. The plant grows best with warm temperatures, plenty of moisture and adequate drainage, but is able to tolerate some drought when mature. Hardiness at least from USDA zone 4 through 9, and other disease resistance is typical of that of other *hibiscus* cultivars.

I claim:

1. A new and distinct cultivar of hardy hybrid *Hibiscus* plant named 'Sultry Kiss' as herein described and illustrated, with heavily overlapped magenta red petals and crimson red eye, mostly three-lobed maple-like foliage with purple tinting and heavily branched stems with burgundy tinting producing a multitude of flowers over at least 12 weeks during the summer and early fall until frost, and suitable as a potted plant; for the garden, and for cut flower arrangements.

* * * * *